United States Patent [19]

Nees

[11] Patent Number: 5,350,318

[45] Date of Patent: Sep. 27, 1994

[54] BIOMEDICAL ELECTRICAL CONNECTOR USING A SOCKET RECEPTACLE HAVING A RESILIENT SHEATH

[75] Inventor: Terry S. Nees, Shoreview, Minn.

[73] Assignee: Minnesota Mining and Manufacturing Company, St. Paul, Minn.

[21] Appl. No.: 133,774

[22] Filed: Oct. 8, 1993

Related U.S. Application Data

[63] Continuation of Ser. No. 661,892, Feb. 27, 1991, abandoned.

[51] Int. Cl.⁵ .................................... H01R 11/22
[52] U.S. Cl. .................................. 439/593; 439/930
[58] Field of Search ............... 439/592, 593, 840, 841, 439/788, 930, 606, 736; 29/883, 876; 128/639–644; 264/265, 278, 279, 301–307, DIG. 60

[56] References Cited

U.S. PATENT DOCUMENTS

| | | | |
|---|---|---|---|
| 839,260 | 12/1906 | Benson | 439/593 |
| 2,623,085 | 12/1952 | Gier, Jr. | 173/259 |
| 2,694,830 | 11/1954 | Pollock | 264/303 |
| 2,972,125 | 2/1961 | Temple et al. | 439/930 |
| 3,165,576 | 1/1965 | Lige | 439/840 |
| 3,587,034 | 6/1971 | Canell | 339/102 |
| 4,027,678 | 6/1977 | van Oostveen | 607/37 |
| 4,192,567 | 3/1980 | Gomolka | 339/75 M |
| 4,205,888 | 6/1980 | Wade | 339/14 R |
| 4,221,457 | 9/1980 | Allen et al. | 339/275 R |
| 4,245,881 | 1/1981 | Michaels | 339/256 R |
| 4,411,277 | 10/1983 | Dickhudt | 128/784 |
| 4,416,498 | 11/1983 | Sado et al. | 439/593 |
| 4,521,365 | 6/1985 | Kurtz | 264/301 |
| 4,632,121 | 12/1986 | Johnson et al. | 128/640 |
| 4,632,496 | 12/1986 | Williams | 339/256 S |
| 4,685,467 | 8/1987 | Cartmell et al. | 128/640 |
| 4,695,241 | 9/1987 | Ventimiglia | 264/301 |
| 4,715,382 | 12/1987 | Strand | 128/640 |
| 4,848,345 | 7/1989 | Zenkich | 128/639 |
| 4,899,754 | 3/1990 | Bly et al. | 128/640 |

Primary Examiner—Neil Abrams
Attorney, Agent, or Firm—Gary L. Griswold; Walter N. Kirn; Jeffrey J. Hohenshell

[57] ABSTRACT

A two component leadwire system is disclosed for electrical connection between biomedical electrodes and electrical equipment for diagnostic or therapeutic use. One leadwire component has a bayonet terminus and can be rugged for reuse. The second leadwire is an inexpensively-made receptacle for making electrical contact with the bayonet. The receptable has a socket for receiving the bayonet and an electrical conductor surrounded by a resilient, insulative sheath. When the bayonet is inserted into the socket, the sheath resiliently grips the bayonet and holds the bayonet in electrical contact with the conductor. A method for making the receptacle components, involving dip molding of the conductor arrayed on a mandril, is also disclosed.

12 Claims, 3 Drawing Sheets

BIOMEDICAL ELECTRICAL CONNECTOR USING A SOCKET RECEPTACLE HAVING A RESILIENT SHEATH

This is a continuation of application Ser. No. 07/661,892 filed Feb. 27, 1991 and now abandoned.

FIELD OF THE INVENTION

This invention relates to biomedical electrical connectors, and particularly an electrical connector using a socket receptacle having electrical contact within a resilient sheath.

BACKGROUND OF THE INVENTION

Modern medicine uses many diagnostic and therapeutic procedures where electrical signals or currents are received or delivered to the patient's body. The interface between medical equipment used in these procedures and the skin of the patient is usually some sort of biomedical electrode. Such an electrode typically includes a conductor which must be connected electrically to the equipment. This connection typically includes a leadwire.

Among the diagnostic and therapeutic procedures using biomedical electrodes are transcutaneous electronic nerve stimulation (TENS) devices used for pain management, neuromuscular stimulation (NMS) used for treating conditions such as scoliosis, and monitors of electrical output from body functions, such as electrocardiagram (ECG) for monitoring heart activity and for diagnosing heart abnormalities.

For each diagnostic or therapeutic procedure, at least one electrode having an electrically conductive gel or adhesive is adhered to the body at the location of interest and electrically connected to diagnostic or therapeutic equipment. Ease of assembly and dissembly of the electrode from electrical connection to the diagnostic or therapeutic equipment is desired. But firm and continuous electrical connection is desired while the diagnostic or therapeutic procedure continues.

For example, in the case of TENS devices, two adhesive-bearing electrodes are adhered to the body where stimulation is desired but must be connected to a generator which provides a series of stimulating electrical pulses.

Conventionally, biomedical electrodes are disposable to preserve sanitary conditions and because such electrodes are generally inexpensive. However, for biomedical electrodes having detachable leadwires, the more expensive leadwires connecting the electrodes to the diagnostic or therapeutic equipment are often intended to be reused.

An example of a disposable electrode, reusable leadwire system is disclosed in coassigned U.S. Pat. No. 4,715,382 (Strand), which shows a disposable electrode adapted to be used with a reusable leadwire having a flat leadwire releasably attachable to a portion of the electrode. Additionally, coassigned U.S. Pat. No. 4,899,754 (Bly et al) discusses an electrode which has specific provision for the removal of the reusable leadwire having a flat contour for releasable insertion into a portion of the flat, conformable biomedical electrode.

Bayonet or male/female electrical connector systems have been developed for electrical devices where secure but releasable connection is desired.

U.S. Pat. No. 4,192,567 (Gomolka); U.S. Pat. No. 4,245,881 (Michaels); and U.S. Pat. No. 4,632,496 (Williams) all disclose electrical connectors where a bayonet or male prong is held within the coils of a helical conductor in a rigid receptacle. The gripping force on the bayonet or male prong is provided by the restoring radial force in the coiled helical conductor, and not by the receptacle housing.

U.S. Pat. No. 4,221,457 (Allen et al) discloses a helical conductor which may be temporarily held in an expanded state, e.g., by solder, but eventually the grip on the male portion of the connection is achieved by the restoring radial force in the radially shrinkable coil member.

U.S. Pat. No. 2,623,085 (Gier, Jr) and U.S. Pat. No. 3,587,034 (Canell) both disclose covers, such as shrouds or caps made of resilient material, about helical or coiled electrical connectors. But the covers provide insulation, not a radial force to grip a male portion of electrical connector.

U.S. Pat. No. 4,205,888 (Wade) discloses an electrical cable surrounded by flexible tubular interlocked metallic armor having a heavy gauge metallic wire connector member helically wound about the armor and serving as a grounding connector at its protecting terminus. Over this metallic construction is a flexible, resilient nonmetallic material serving as a sleeve to secure the cable construction to an electrical panel. The side walls of the sleeve tightly engage the side walls of the armored cable to provide a substantially permanent connection.

Care should be taken to provide a means electrical connection which will not damage normally reusable leadwires due to excessive handling.

SUMMARY OF THE INVENTION

The art of electrical connection of disposable components to reusable electrical equipment needs a means of electrical connection which minimizes expense, maximizes ease of electrical connection, and provides firm but detachable electrical connection during use.

The problems found in the art are solved by the present invention which provides a two component leadwire system which provides facile yet firm electrical connection between disposable electrodes and more expensive biomedical electrical equipment.

One component of the leadwire is connected, either permanently or releasably, to the durable and reusable electrical equipment. At the other end, that first component of the leadwire system has a bayonet terminus, such as a pin or prong of cylindrical or angular geometrical radial profile.

The second component of the leadwire is connected, either permanently or releasably, to the disposable biomedical electrode. At the other end, that second component provides a socket receptacle for electrical connection with the bayonet terminus of the first component. The receptacle has an electrical conductor, for electrical contact at at least one point. The receptacle also has a radial gripping force provided by a resilient sheath formed about the electrical conductor, which may be coiled to surround the bayonet or in collinear alignment with the bayonet.

The first component can be constructed of materials sufficiently rugged to permit repeated use of the first component for electrical connection for diagnostic or therapeutic uses.

The second component can be constructed of materials to provide for reuse. However, it is preferred to use inexpensive materials to permit disposal of the second component after use, either separate from together with the disposable biomedical electrode.

Thus, one aspect of the present invention is a very inexpensive second component, which is a receptacle for making electrical contact with a bayonet connector. The receptacle comprises a socket for receiving the bayonet connector. The socket comprises an electrical conductor surrounded by a resilient, insulative sheath, whereby when the bayonet connector is inserted into the socket, the sheath resiliently grips the bayonet connector, holding the bayonet connector in electrical contact with the conductor.

Another aspect of the present invention is that the receptacle of the present invention includes a conductor surrounded by a resilient, insulative sheath. The sheath has a blind end bore, conveniently placed near one end. The bore is defined by an inner wall, which the electrical conductor penetrates so that it protrudes into the bore to at least one point, such that when the bayonet connector is inserted into the bore, the sheath resiliently grips the bayonet connector, holding the bayonet connector in electrical contact with the conductor.

A further aspect of the present invention is a two component leadwire system between a biomedical electrode and electrical equipment for diagnostic or therapeutic use. The leadwire system comprises a first leadwire component in electrical contact with the electrical equipment and a second leadwire component in releasable electrical contact the first leadwire component and also in electrical contact with the biomedical electrode. The first leadwire component has an electrically conductive bayonet terminus, and the second leadwire component has a socket for receiving the bayonet terminus. The socket comprises an electrical conductor surrounded by a resilient, insulative sheath, whereby when the bayonet terminus is inserted into the socket, the sheath resiliently grips the bayonet terminus, holding said bayonet terminus in electrical contact with the electrical conductor.

Conveniently, the receptacle of the present invention is fabricated by dip molding, so that the resilient, insulative sheath is formed from a polyvinyl chloride plastisol. In one embodiment, a portion of conductor is shaped into a coil concentric with the bore, so that when the bayonet connector is inserted into the bore, the bayonet connector is contained within the coil. This facilitates manufacture and provides at least one point and preferably multiple points for electrical contact between the conductor and the bayonet.

In a second embodiment the electrical conductor is not coiled but is in collinear alignment with the bore, so that when the bayonet connector is inserted into the bore, the bayonet connector slides and rests against the electrical connector.

The invention can also be viewed as a method for forming a socket receptable for facile electrical connection. The method employs providing an elongated conductor and a mandril, attaching at least one end of the conductor to the mandril in a releasable manner, dipping the mandril in a plastisol, forming a coating of plastisol on the mandril and at least a portion of the conductor, curing the coating, and stripping the receptacle from the mandril. In the described method, the attaching step is conveniently performed either by coiling one end of the conductor about the mandril or by using magnetized connection points at opposite ends of the mandril. In some embodiments of the method, the step of heating the conductor and mandril prior to the dipping step will be performed, because this facilitates the formation of a gel of plastisol on the mandril and conductor during the dipping step. Desirably, the plastisol is a dispersion of polyvinyl chloride.

The invention provides a receptacle for making electrical contact with a bayonet connector. The electrical connection is easy to connect and disconnect but provides a firm albeit detachable electrical connection during diagnostic or therapeutic use. The means of electrical connection preferably provides a reusable leadwire component for electrical connection to equipment and an inexpensive leadwire component for electrical connection to disposable biomedical electrodes.

A feature of the invention is that the radial force which grips the bayonet terminus of the first leadwire component and which presses the electrical conductor in the socket receptacle of the second leadwire component against the bayonet terminus is provided by the resilience of the sheath, rather than any spring force exerted by the coiled or collinearly aligned conductor. Thus, the conductor need not be made of a metallic spring material nor be manufactured in a manner to provide an engaging helical force by the conductor itself.

Thus, it is an advantage of the invention that socket receptacles formed according to the present invention are very inexpensive, and thus suitable for use in assemblies that must be disposed of after use.

BRIEF DESCRIPTION OF THE DRAWING

A more complete understanding of the invention and its advantages will be apparent from the Embodiments of the Invention below taken in conjunction with the accompanying Drawings, in which.

EMBODIMENTS OF THE INVENTION

Figure 1:
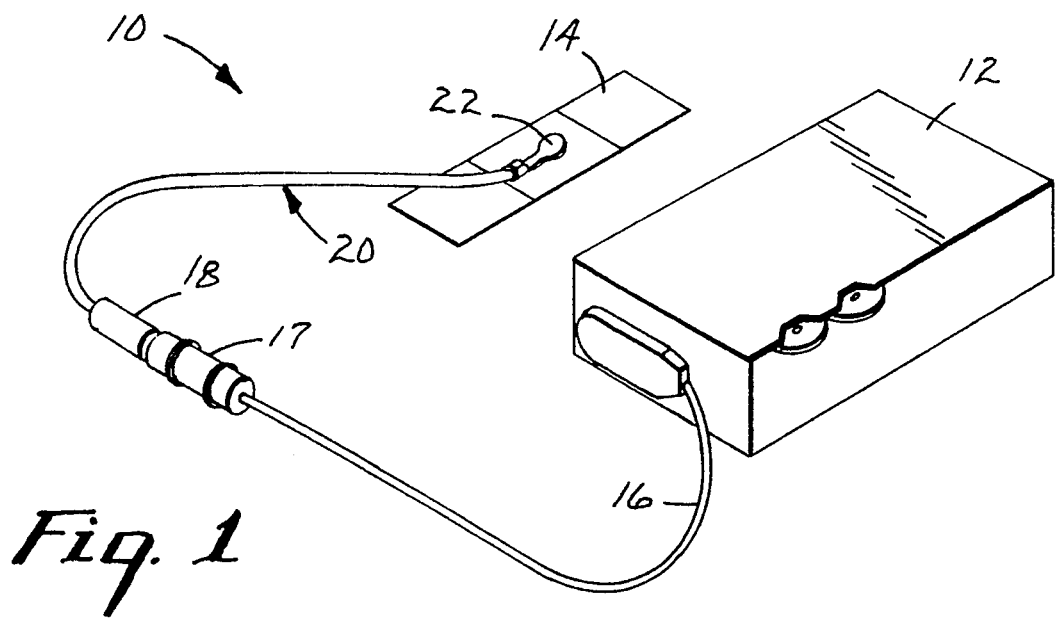
FIG. 1 illustrates a perspective view of a leadwire system according to the present invention as part of a therapeutic system for connecting a stimulator to a patient contacting electrode.

FIG. 1 illustrates a perspective view of a leadwire system according to the present invention as part of a system for connecting a stimulator to a patient contacting electrode. The therapeutic system 10 includes a stimulator 12 placed in electrical contact with an electrode 14 via a first leadwire component 16 ending in a bayonet portion 17 having a pin-shaped terminus, (not seen) inserted into the socket portion 18 of a receptacle leadwire component 20.

Figure 2:
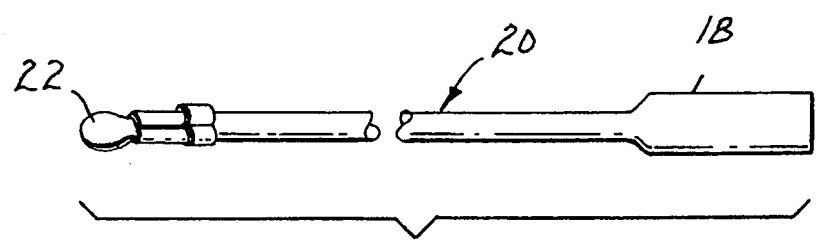
FIG. 2 illustrates a side view of the receptacle leadwire component in isolation.

FIG. 2 illustrates a side view of the receptacle component 20. The receptacle component 20 includes a socket portion 18 and an electrode terminal portion 22, shown here as a crimp-on spade. It is to be understood that many different types of terminal portions are considered within the scope of the invention, depending on the exact type of end use contemplated. For some purposes, including pre-wired electrodes, the bared electrical conductor alone may be appropriate.

Figure 3:
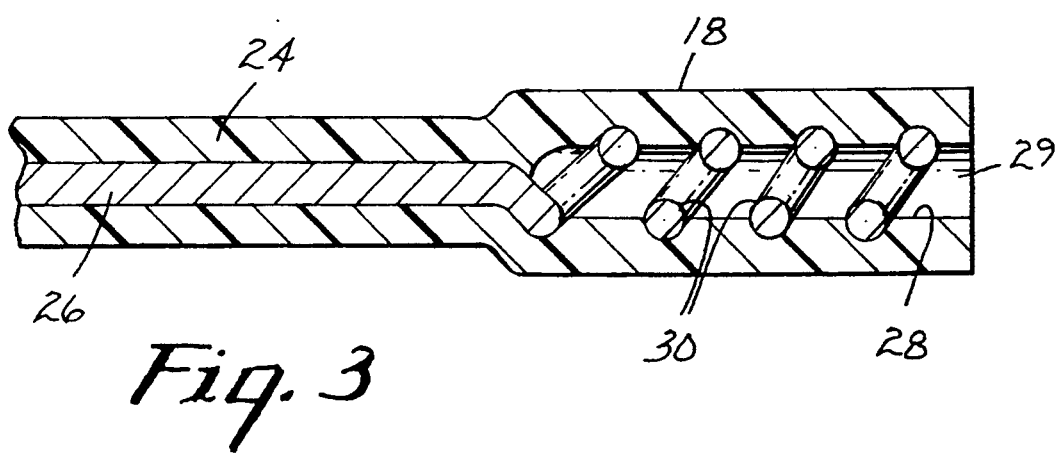
FIG. 3 illustrates a cross section view of the receptacle leadwire component of FIG. 2.

FIG. 3 illustrates a cross section view of the socket portion 18 of the receptacle component 20 of FIG. 2. A resilient, insulative sheath 24 surrounds an electrical conductor 26, which sheath has an inner wall 28 surrounding a bore 29 within the socket portion 18, where the conductor 26 has been wound into a coil 30. The coil 30 protrudes the inner wall 28 at at least one point and is exposed to the bore 29 for contact with a bayonet terminus of first leadwire component 16 which may be inserted into the bore.

Figure 4:
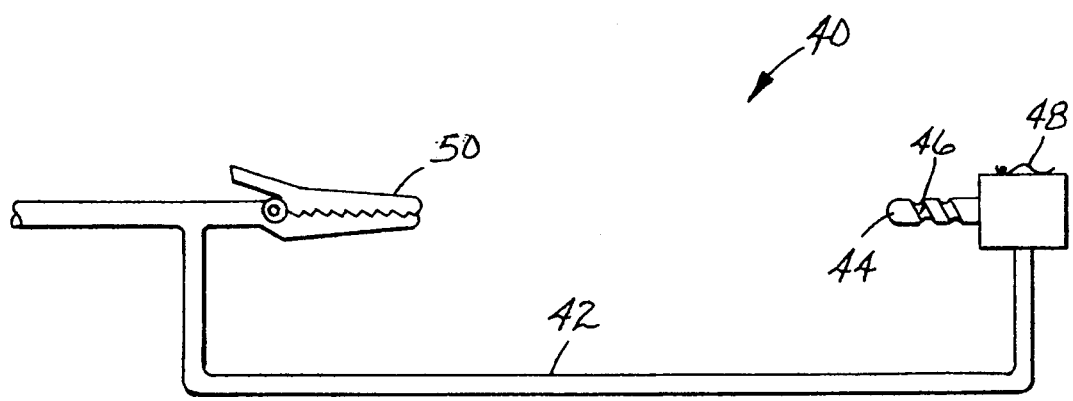
FIG. 4 illustrates a dipping mandril appropriate for forming the receptacle leadwire component of FIG. 2.

FIG. 4 illustrates a dipping mandril appropriate for forming the receptacle of FIG. 2. The mandril 40 may include a rod 42 having a projection 44, which may have a recess 46 thereon for preparing the coil 30 of the electrical conductor 26. Preferably, the recess 46 is in the shape of a helix. Preferably, the mandril 40 is provided with a spring clip 48 and a clamp 50 to hold the electrical conductor 26 during the dipping process.

Figure 5:
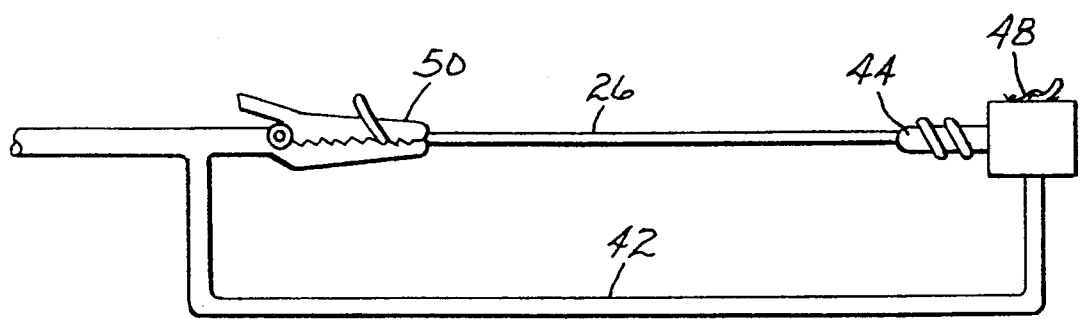
FIG. 5 illustrates the dipping mandril of FIG. 4, shown with a conductor positioned for the dipping step.

FIG. 5 illustrates the use of the dipping mandril 40 of FIG. 4 with an electrical conductor 26, preferably a metallic electrical wire positioned for the dipping step, gripped adjacent its ends by the spring clip 48 and the clamp 50.

Figure 6:
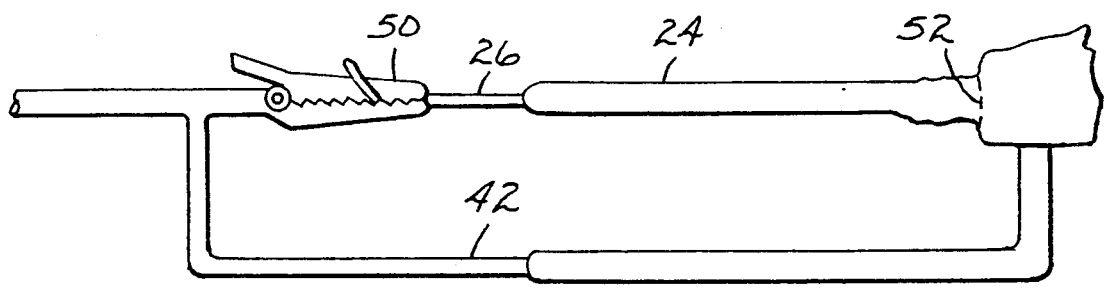
FIG. 6 illustrates the dipping mandril of FIG. 5 after it has been dipped in plastisol, and the coating thus created has been cured.

FIG. 6 illustrates the effect of dipping mandril 40 of FIG. 5 in plastisol and the effect of curing the plastisol about the electrical conductor 26 having coil 30. With a cutting tool (not shown) the receptable component 20, having sheath 24 surrounding and providing resiliency for electrical coil 30, is cut at cut area 52 and fashioned to expose bore 29 at the socket portion 18. After the finished receptacle component 20 is released from the mandril 40, the electrode terminal portion 22 is completed as desired for connection with disposable biomedical patient electrode 14.

Figure 7:
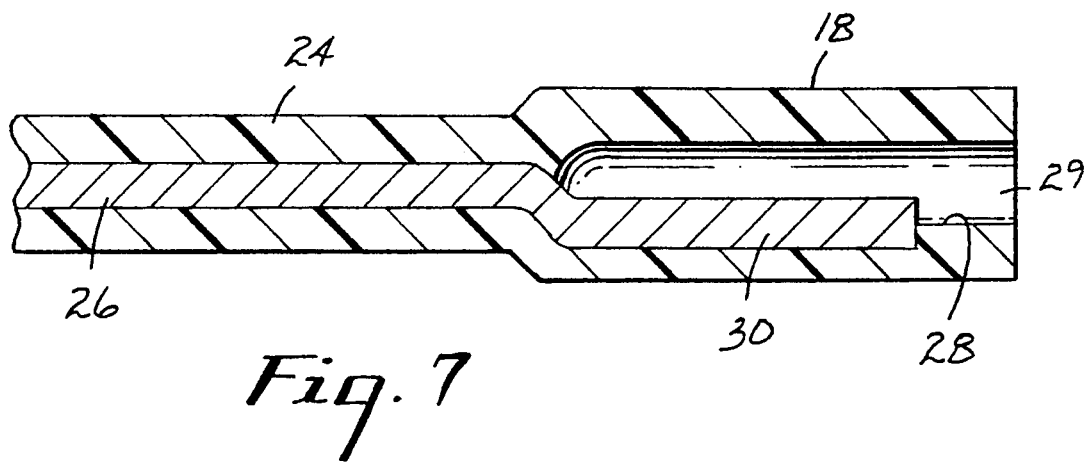
FIG. 7 illustrates a cross section view of an alternate embodiment of the receptacle leadwire component of FIG. 2.

FIG. 7 illustrates a cross section view of an alternate embodiment of the socket portion 18 of the receptacle component 20 of FIG. 2. In this embodiment, the conductor 26 is not coiled, but is generally collinear with the axis of the receptacle component 20 and the bayonet after insertion into bore 29. A portion of the conductor 26 is exposed within the bore 29 for contact with a bayonet terminus of the first leadwire component 16 which may be inserted into the bore 29.

Figure 8:
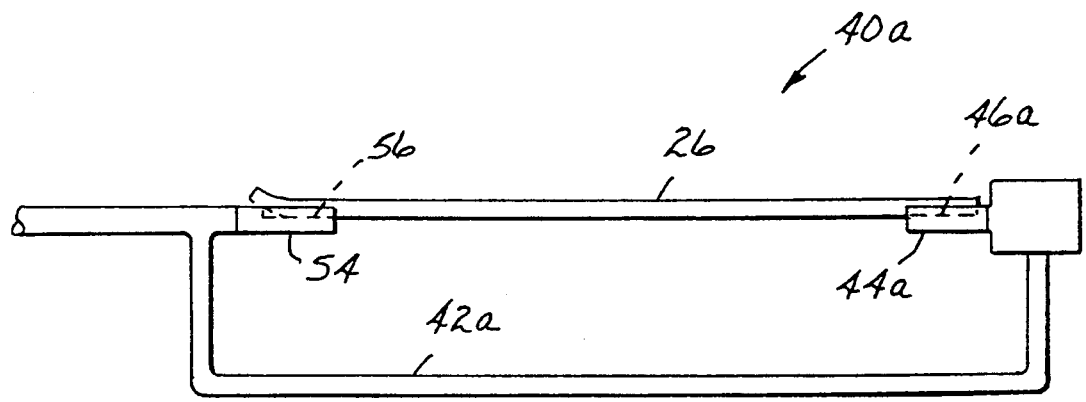
FIG. 8 illustrates a dipping mandril for forming the receptacle leadwire component of FIG. 7.

FIG. 8 illustrates an alternate embodiment of a dipping mandril appropriate for forming the receptacle of FIG. 7. The mandril 40a may include a rod 42a having a projection 44a, which will have a recess 46a thereon which is generally collinear with the axis of the rod 42a. Preferably, the mandril 40a is provided with a protrusion 54 which may have a recess 56 thereon. In this embodiment, the projection 44a and the protrusion 54 may be magnetized, so that if the conductor 26 is made from a ferromagnetic material, (e.g. stainless steel yarn), the fabrication of the receptacle component 20 simplified: when the conductor 26 can magnetically adhere to the mandril, the labor of setting up the mandril for dipping is reduced.

The first leadwire component 16 can be made from electrically conductive materials having an insulating cover about the length of component 16, terminating at electrical equipment with a connector adapted for mating with the particular electrical equipment employed in a diagnostic or therapeutic use. At bayonet portion 17, a bayonet pin made of rugged electrically conductive material is sized for releasable contact with coil 30 within resilient sheath Preferably, a single strand, multi-strand copper wire, or particularly preferred, tinsel wire (commercially available as 0.03 conductor O.D. nominal conductor wire from Montgomery Wire of Windsor Locks, Conn.) used for the leadwire in component 16 with a bayonet pin made of nickel plated brass soldered or crimped to the copper wire.

The electrical conductor 26 of the receptacle component 20 may be made from many different conductive materials, with single strand or multi-strand copper wire of 24 gauge being considered particularly preferred. Stainless steel filament yarn such as "Bekinox VN" yarn (commercially available from Bekaert Corporation, of Belgium, with U.S. offices in Marietta, Ga.) is also expected to be suitable, particularly when mandril 40a is used.

Plastisols suitable for forming the resilient, insulative sheath 24 can include dispersion grade polyvinyl chloride homopolymer in suspension with a plasticizer such as dioctyl phthalate and a heat stabilizer such as cadmium stearate or dioctyl tin maleate. Variations on these ingredients, as well as the use of additives such as pigments and secondary stabilizers are well known to those with skill in the plastisol blending art. Process variables such as time and temperature of the pre-heating or the cure are also well known to those with skill in the plastisol blending art. Preferably, the resilient, insulative sheath 24 is made of polyvinyl chloride polymer, cured from plastisol covering the mandril and wire and having the following properties:

| | |
| --- | --- |
| Durometer | 78 +/− Shore A scale |
| Tensile strength | 141 kg/cm$^2$ minimum |
| Percent elongation | 350% minimum |
| Tear strength | 37.5 kg/cm minimum |
| Specific gravity | 1.183 +/− 0.005 |

Usefulness of the Invention

The leadwire component system of the present invention permits the retention of a rugged portion of a leadwire having a bayonet terminus which can withstand repeated connections and disconnections but avoids the point of connection at the biomedical electrode. The receptable component is made inexpensively but provides a facile yet firm electrical connection at the bayonet/socket junction. Further, because the receptacle component is disposable, any type of connection of receptacle component to a disposable biomedical electrode can be accommodated without sacrificing the reusable qualities of the first leadwire component terminating at a bayonet pin.

Thus, an inexpensive connection between the biomedical electrode and a component of the leadwire system is now possible. Further, a terminus of a reusable leadwire component is not subjected to repeated or attempted placement within layers of a biomedical electrode because that component can now be replaced by the receptacle leadwire component of the present invention.

The invention is not limited to biomedical electrodes and diagnostic or therapeutic electrical equipment. Any electrical connection where an inexpensive or disposable terminal requires facile but firm electrical connection to a more expensive, elaborate, or complicated electrical equipment can benefit from the invention.

For a greater appreciation of the invention, the following examples further illustrate embodiments of the invention.

EXAMPLE 1

A dipping mandril generally as shown in FIG. 4 was fabricated from stainless steel with a projection having an outside diameter of 0.072 inches (0.18 cm), having shallow recesses making two coils. A wire formed as a single strand of 0.025 (0.06 cm) of copper was wrapped around the projection generally as shown in FIG. 5. The mandril with wire about the projection and extending to the clamp was dipped at room temperature into a plastisol commercially available as compound 95190, color 805 (beige) from Lakeside Plastics of Oshkosh, WI. Compound 95190 plastisol yields a polyvinyl chloride polymer having the following properties: Durometer of 78±3 Shore A scale; Tensile strength of 141 kg/cm$^2$ minimum; Percent elongation of 350% minimum; Tear strength of 37.5 kg/cm minimum; and Specific gravity of 1.18±0.005. The mandril and wire were coated with the plastisol. The plastisol was cured in a convection oven at about 375° F. (190° C.) for about 6 minutes. After cooling, the finished receptacle component was cut from the mandril with a wire stripping tool to reveal an inner wall about a bore. The electrical conductor penetrates inner wall and protrudes into said bore at at least one point for establishing electrical contact with a metallic bayonet terminus,.

EXAMPLE 2

Receptacle components made according to Example 1 were tested by inserting a 0.20 cm diameter cylindrical bayonet terminus (made of nickel plated brass and commercially available from Minnesota Wire and Cable of St. Paul, Minn.) into the socket portion of the receptacle component. The insertion forces noted were about 9 to 13 Newtons, and the withdrawal forces noted were about 22 to 31 Newtons. Thus, the resilient insulative sheath of the socket portion of the receptacle component confined the coil of the electrical conductor in such a manner that more force would be needed to remove the cylindrical bayonet terminus than to insert the bayonet terminus. The connection between the nickel plated brass bayonet terminus and the copper coil was facilely, yet releasably firmly performed, using a receptacle component inexpensively made. The resilient sheath provided the radial gripping force to firmly electrically connect the bayonet terminus within the coil.

EXAMPLE 3

A dipping mandril generally as shown in FIG. 8 is fabricated from stainless steel and the projection and the protrusion are magnetized. A length of stainless steel filament yarn commercially available as "Bekinox VN" yarn from Bekaert Corporation of Marietta, Ga. is held magnetically within the recesses on the projection and the protrusion. The mandril is then dipped and the finished receptacle component is cut from the mandril as described in Example 1.

While certain embodiments of the present invention have been described in detail herein and as shown in the accompanying Drawing, it will be evident that various further modifications are possible without departing from the scope of the invention. For example, while the formation of the receptacle component of the present invention by means of plastisol dip molding advantageously serves to insulate a length of wire used as the conductor, one could also form the receptacle from insulated wire having a bared end and then attaching that end (e.g. by coiling) to the core pin of an injection mold and then injection molding a resilient insulated sheath around the bared end. Also, it will be apparent that the artisan may vary the parameters of mandril projection size, number of coils, sheath thickness, and sheath material durometer to obtain different results with different sizes of bayonet terminii.

What is claimed is:

1. A receptacle for making electrical contact with a bayonet connector, comprising:
a dip molded socket for receiving the bayonet connector comprising an electrical conductor surrounded by a resilient, insulative sheath, wherein said socket is formed by dip molding said sheath from a plastisol about said electrical conductor, and whereby when the bayonet connector is inserted into said socket, said sheath resiliently grips the bayonet connector, holding the bayonet connector in electrical contact with said conductor.

2. The receptacle according to claim 1, wherein said resilient insulative sheath comprises polyvinyl chloride.

3. The receptacle according to claim 1, wherein said electrical conductor has at least one point protruding from said sheath into said socket.

4. The receptacle according to claim 1, wherein said sheath has an inner wall about a bore, and wherein said electrical conductor penetrates said inner wall and protrudes into said bore at at least one point for establishing electrical contact with the bayonet connector.

5. The receptacle according to claim 4, wherein a portion of said electrical conductor is shaped into a coil concentric with and protruding into said bore, so that when the bayonet connector is inserted into said bore, the bayonet connector is contained within said coil and in electrical contact at at least one point.

6. The receptacle according to claim 1, wherein said sheath comprises a polymer having a Shore A Durometer of about 78 Shore A, a Tensile Strength of at least about 141 kg/cm$^2$, and a Percent Elongation of at least 350%.

7.) A two component leadwire system between a biomedical electrode and electrical equipment for diagnostic or therapeutic use, comprising:
a first leadwire component in electrical contact with the electrical equipment, and
a second leadwire component in releasable electrical contact with said first leadwire component and also in electrical contact with the biomedical electrode,
said first leadwire component having an electrically conductive bayonet terminus, and
said second leadwire component having a did molded socket for receiving said bayonet terminus, said socket comprising an electrical conductor surrounded by a resilient, insulative sheath, wherein said socket is formed by dip molding said sheath from a plastisol about said electrical conductor, and whereby when said bayonet terminus is inserted into said socket, said sheath resiliently grips said bayonet terminus, holding said bayonet terminus in electrical contact with said electrical conductor.

8. The two component leadwire system according to claim 7, wherein said resilient insulative sheath comprises polyvinyl chloride.

9. The two component leadwire system according to claim 7, wherein said electrical conductor has at least one point protruding from said sheath into said socket.

10. The two component leadwire system according to claim 7, wherein said sheath has an inner wall about a bore, and wherein said electrical conductor penetrates said inner wall and protrudes into said bore at at least one point establishing electrical contact with the bayonet connector.

11. The two component leadwire system according to claim 10, wherein a portion of said electrical conductor is shaped into a coil concentric with and protruding into said bore, so that when the bayonet connector is inserted into said bore, the bayonet connector is contained within said coil and in electrical contact at at least one point.

12. The two component leadwire system according to claim 7, wherein said sheath comprises a polymer having a Shore A Durometer of about 78 Shore A, a Tensile Strength of at least about 141 kg/cm$^2$, and a Percent Elongation of at least 350%.

* * * * *

UNITED STATES PATENT AND TRADEMARK OFFICE
CERTIFICATE OF CORRECTION

PATENT NO.: 5,350,318

DATED: September 27, 1994

INVENTOR(S): Terry S. Nees

It is certified that error appears in the above-identified patent and that said Letters Patent is hereby corrected as shown below:

Col. 2, line 24, "protecting" should read --projecting--.

Col. 2, line 29, after "means" insert --of--.

Col. 3, line 43, after "of" insert --the--.

Col. 5, line 60, after "20" insert --is--.

Col. 6, line 4, after "sheath" insert --24--.

Col. 6, line 36, after "78 +/-" insert --3--.

Col. 7, line 23, after "1.18" insert --3--.

Signed and Sealed this

Sixteenth Day of April, 1996

Attest:

BRUCE LEHMAN

Attesting Officer

Commissioner of Patents and Trademarks